United States Patent
Schnitzler et al.

(10) Patent No.: US 9,603,653 B2
(45) Date of Patent: Mar. 28, 2017

(54) APPARATUS FOR COAGULATING TISSUE

(75) Inventors: Uwe Schnitzler, Tubingen (DE); Daniel Schaller, Tubingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 2378 days.

(21) Appl. No.: 10/577,297

(22) PCT Filed: Oct. 28, 2004

(86) PCT No.: PCT/EP2004/012212
§ 371 (c)(1),
(2), (4) Date: Apr. 27, 2006

(87) PCT Pub. No.: WO2005/041800
PCT Pub. Date: May 12, 2005

(65) Prior Publication Data
US 2007/0149970 A1    Jun. 28, 2007

(30) Foreign Application Priority Data
Oct. 30, 2003 (DE) .................. 103 50 709

(51) Int. Cl.
*A61B 18/14* (2006.01)
*A61B 18/04* (2006.01)
*A61B 18/00* (2006.01)

(52) U.S. Cl.
CPC .......... *A61B 18/14* (2013.01); *A61B 18/042* (2013.01); *A61B 2018/00196* (2013.01); *A61B 2018/00583* (2013.01); *A61B 2018/00589* (2013.01); *A61B 2018/00601* (2013.01); *A61B 2018/00607* (2013.01); *A61B 2018/00791* (2013.01); *A61B 2018/1475* (2013.01)

(58) Field of Classification Search
USPC .............................. 606/32–50; 607/115–116
See application file for complete search history.

(56) References Cited

U.S. PATENT DOCUMENTS

| 2,828,748 A | 4/1958 | August |
| 5,088,997 A | 2/1992 | Delahuerga et al. |

(Continued)

FOREIGN PATENT DOCUMENTS

| DE | 41 39 029 | 6/1993 |
| DE | 198 20 240 | 12/1999 |
| JP | 2002-301088 A | 10/2002 |

OTHER PUBLICATIONS

Machine Translation of JP 2002-301088-A, Printed Oct. 19, 2010.*
Translation of JP 2002301088 from Nov. 2011, orginial Japanese patent published Aug. 15, 2002, pp. 1-41.*

*Primary Examiner* — Ronald Hupczey, Jr.
(74) *Attorney, Agent, or Firm* — Blank Rome LLP

(57) ABSTRACT

For the coagulation of tissue there are known instruments, in particular probes, that are designed to deliver argon gas into a space between an electrode within the probe and the tissue. In some cases the intention is to coagulate tissues situated at the side of the outlet of the probe. The invention provides an apparatus for coagulating tissue in which the distal end of the electrode projects out of the gas-delivering device or probe, and at said distal end a guiding device for directing and guiding the gas or plasma is disposed in such a way that at least part of the flowing gas or plasma is deflected into a predetermined direction.

16 Claims, 1 Drawing Sheet

(56) References Cited

U.S. PATENT DOCUMENTS

| | | | |
|---|---|---|---|
| 5,244,462 A | | 9/1993 | Delahuerga et al. |
| 5,449,356 A | * | 9/1995 | Walbrink et al. ............... 606/49 |
| 5,902,328 A | * | 5/1999 | LaFontaine et al. ......... 607/116 |
| 6,039,736 A | | 3/2000 | Platt, Jr. |
| 6,112,123 A | | 8/2000 | Kelleher et al. |
| 6,142,995 A | | 11/2000 | Cosmescu |
| 6,149,648 A | * | 11/2000 | Cosmescu ...................... 606/42 |
| 6,197,026 B1 | | 3/2001 | Farin et al. |
| 6,602,249 B1 | * | 8/2003 | Stoddard et al. ............... 606/45 |
| 2003/0065324 A1 | | 4/2003 | Platt |

\* cited by examiner

APPARATUS FOR COAGULATING TISSUE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to an apparatus for coagulating tissue.

BACKGROUND OF THE INVENTION

Such an apparatus is known, for instance, from document DE 41 390 29 A1. In this apparatus a gas flows axially from an outflow opening of a gas-delivering device to an electrode, and the electrode is positioned in front of the opening, so that a plasma tends to be produced in a direction axial to the gas-delivering device. Especially when an endoscopic operation is being performed within a body cavity, i.e. under confined conditions, it is difficult to coagulate tissue sites situated at the side, in a direction radial with respect to the opening.

The document DE 198 202 40 C2 discloses a tissue-coagulating apparatus in which the electrode is disposed entirely within a tubular probe provided with a slit-shaped opening that passes helically around its circumference, so that the delivered gas and also the plasma emerge in a direction radial to the probe. One problem here resides in manufacturing such probes, in view of the confined spatial relationships. Another is that the probe material can relatively easily be damaged by the high temperatures of the plasma.

BRIEF SUMMARY OF THE INVENTION

It is an object of the invention to an apparatus for coagulating tissue such that by simple means it becomes possible reliably to specify a direction of the plasma beam that deviates from an axial direction.

This object is achieved by an apparatus according to the present invention comprising an HF generator, an electrode connected to said HF generator and adapted to produce a high-frequency current, a gas-delivering device defining an outlet and adapted to deliver, in use, an inert gas from said outlet of said gas-delivering device into a space defined between said electrode and said tissue such that between said electrode and said tissue a plasma is produced, a distal end of said electrode projecting out of said gas-delivering device, and a guiding device for directing and guiding at least one of said gas and said plasma is disposed at said distal end of said electrode and adapted such that at least a part of said at least one flowing gas and plasma is diverted into a predetermined direction.

The success of the invention resides in the fact that the electrode itself is structurally included in the overall mechanical construction of the device, in that it to some extent carries part of the gas-delivering device, namely the guiding device. The preferred direction of the gas or plasma is thus determined by the guiding device. It should be pointed out here that within a space completely filled with an inert gas, the direction in which the plasma is generated is not influenced by flow of the gas. However, because the plasma always appears along the path of least overall resistance, and it is practically impossible for the space to be filled entirely homogeneously, even in a body cavity, on one hand it is possible by way of the guiding device to specify the gas current and hence the gas concentration within the space, and on the other hand the desired change of direction can be brought about by an extension of the path the plasma must follow from the electrode to the tissue.

Preferably the guiding device consists of an electrically insulating material, as a result of which the above-mentioned change of path is facilitated.

Furthermore, the guiding devices preferably are made of a thermally stable material, so that during an operation, even if the guiding device is in prolonged contact with the plasma, there are no damaging alterations of the material. A particularly suitable material is a ceramic, which can be applied for instance by spraying on or by dipping.

The electrode is preferably constructed in the form of a rod or wire, as is known per se, while the guiding device is preferably disposed in an axially symmetric manner around the electrode, in such a way that the gas/plasma flows into the surrounding space substantially radially with respect to the outlet of the gas-delivering device. This arrangement makes it unnecessary for the apparatus to be rotated within a body cavity during an endoscopic operation in order to coagulate regions of tissue situated radial to the outlet. All that is needed is to bring the apparatus into the vicinity of the tissue site to be coagulated, because the plasma (as explained above) seeks out the shortest and hence lowest-resistance path. The plasma current does not change direction until the plasma path is lengthened, when the treated tissue dries out and hence in turn acquires a higher resistance.

The guiding device is preferably made concave on its side that faces the outlet, as a result of which a diversion of the gas stream that favors its flow is accomplished in an especially simple manner.

To prevent mechanical injury caused by touching the tissue, the guiding device is rounded on its side that faces away from the outlet. The guiding device thus simultaneously constitutes a form of protection against direct contact between electrode and tissue, which could have fatal consequences, as is well known.

The electrode in one preferred embodiment of the invention is made movable relative to the outlet, in such a way that when it is in a retracted state, the guiding device closes the outlet in a substantially leakproof manner. This can ensure that during introduction of the probe no body fluid or other contaminants can enter the gas-delivering device.

In the following, preferred embodiments of the invention are described in greater detail and by way of example with reference to the accompanying drawing

DETAILED DESCRIPTION OF THE INVENTION

Figure 1:
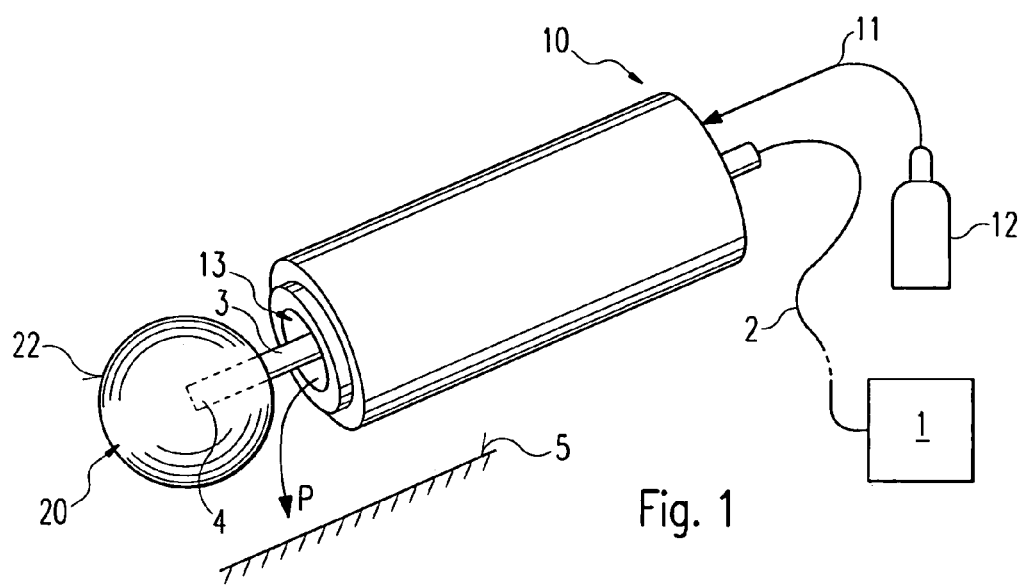
FIG. 1 shows a perspective view of a first preferred embodiment of the invention, with peripheral devices indicated schematically.

In the following description, the same reference numerals are used for identical parts or parts with identical actions.

FIG. 1 shows an end piece of a probe, comprising a gas-delivering device 10 in the shape of a tube, the lumen of which communicates with a gas source 12 by way of a conduit 11. An electrode 3 (ordinarily made of tungsten) is disposed substantially coaxially within the gas-delivering device 10, and is connected to an HF generator by way of an electrical conductor 2. A distal end 4 of the electrode 3 projects outward through an outlet 13 of the gas-delivering device.

Attached to the distal end 4 of the electrode 3 in the embodiment of the invention shown in FIG. 1 is a spherical ceramic part that forms a guiding device 20. A stream of inert gas, supplied by the gas source 12 and emerging from the outlet 13, is diverted by this arrangement into the direction indicated by the arrow P. If the arrangement is positioned near and parallel to a tissue surface 5, the space delimited by the guiding device 20 in combination with the end-region of the gas-delivering device 10, at its outlet 13, is restricted sufficiently that when the supplied inert gas is ionized by a high-frequency current coming from the generator 1, the shortest path available to the resulting plasma between the electrode 3 and the tissue surface 5 is oriented radially with respect to the electrode 3. As a result, the guiding device 20 serves not only to determine the direction of flow of the supplied inert gas, but also to "guide" the plasma.

Figure 2:
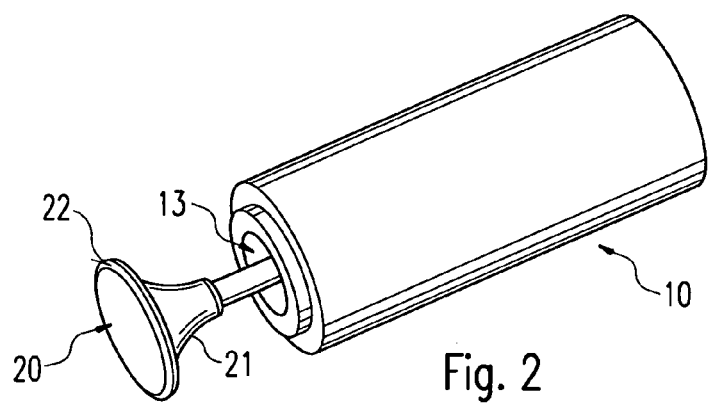
FIG. 2 shows a second preferred embodiment of the invention, in a drawing similar to that in FIG. 1.

The embodiment of the invention shown in FIG. 2 differs from the embodiment in FIG. 1 in that the guiding device 20 is not spherical but rather is shaped like a valve for an internal combustion engine, comprising a concave inner section 21 in the region opposite the outlet 13 of the gas-delivering device 10. The distal end of the guiding device, facing away from the gas-delivering device 10, is flattened. The transitional region between the flattened distal section and the inner section 21 has a rounded contour 22 such that no mechanical damage to the tissue can be caused by contact with the tissue surface 5.

Figure 3:
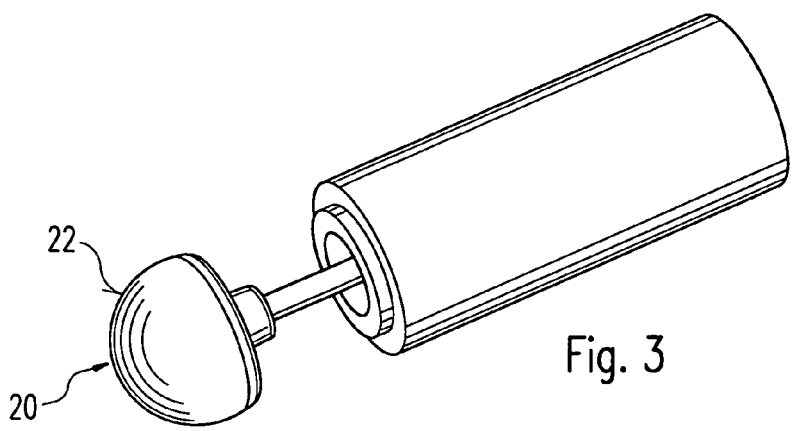
FIG. 3 shows a third embodiment of the invention, in a drawing corresponding to that in FIG. 2.

The embodiment of the invention shown in FIG. 3 differs from the embodiment in FIG. 2 in that instead of being flat, the distal section of the guiding device 20 is hemispherical, and thus as a whole constitutes a rounded contour 22 that likewise reduces the risk of injury.

The electrode 3 can be made retractable and/or can be pushed forward, out of the outlet 13, so that when the electrode 3 is in the retracted state the guiding device 20 is seated on the outlet 13. This positioning avoids the danger that during insertion of the gas-delivering device 10 or a correspondingly designed probe, body fluid or the like will enter the lumen of the gas-delivering device 10, because when in this state the outlet 13 is closed.

LIST OF REFERENCE NUMERALS

1 HF generator
2 Electrical conductor
3 Electrode
4 Distal end
5 Tissue surface
10 Gas-delivering device
11 Conduit
12 Gas source
13 Outlet
20 Guiding device
21 Inner section
22 Rounded contour

The invention claimed is:

1. An apparatus for coagulating tissue, comprising:
an electrode adapted to produce a high-frequency current;
a gas-delivering device having an outlet and being adapted to deliver an inert gas from said outlet into a space defined between said electrode and said tissue, such that a plasma is produced between said electrode and said tissue when said high-frequency current is applied to said inert gas, wherein a distal end of said electrode projects out of said outlet of said gas-delivering device; and
a guiding device comprised of an electrically insulating material and disposed at said distal end of said electrode, said guiding device for directing and guiding said plasma such that at least a part of said plasma is diverted in a predetermined direction,
wherein a cross-section of at least a portion of said guiding device is at least a size of an opening of said outlet at a furthest distal end of said gas-delivering device in order to divert said plasma into said space substantially radially with respect to an opening of said outlet of said gas-delivering device,
wherein the guiding device comprises a concave surface at a surface facing the outlet of the gas-delivering device and a substantially hemispherical surface at a surface facing away from the outlet of the gas-delivering device, and
wherein only the electrode and the guiding device, and no other portion, of the apparatus extend past the opening of said outlet at said furthest distal end of the gas-delivering device.

2. The apparatus according to claim 1, wherein said guiding device is comprised of a thermally stable material.

3. The apparatus according to claim 1, wherein said substantially hemispherical surface of said guiding device prevents mechanical damage if said guiding device touches said tissue.

4. The apparatus according to claim 1, wherein said electrode is movable relative to said outlet such that when said electrode is moved into a retracted position said guiding device closes said opening of said outlet at the furthest distal end of said gas-delivering device in a substantially leakproof manner.

5. The apparatus according to claim 1, wherein the cross-section of at least a portion of said guiding device is larger than the size of said opening of said outlet.

6. The apparatus according to claim 1, wherein a diameter of the cross-section of at least a portion of said guiding device is larger than a diameter of said opening of said outlet.

7. The apparatus of claim 1, wherein the electrode is configured such that it may be retracted and pushed forward with respect to the gas-delivering device.

8. The apparatus of claim 1, wherein the guiding device is ceramic.

9. An apparatus for argon-plasma coagulating tissue, comprising:
a gas-delivering device;
an electrode disposed substantially coaxially with the gas-delivering device and configured to generate a high-frequency current, wherein a distal end of the electrode projects outward through an outlet of the gas-delivering device; and a guiding device disposed at the distal end of the electrode, wherein the guiding device is configured for guiding a plasma stream exiting the gas-delivering device, the plasma stream being produced when said high-frequency current is applied to an inert gas delivered by the gas-delivering device, wherein the guiding device is comprised of a material that is electrically insulating and thermally stable, wherein the guiding device is disposed in an axially symmetric manner around the distal end of the electrode and a cross-section of at least a portion of said guiding device is at least a size of an opening of said outlet at a furthest distal end of the gas-delivering device in order to divert the plasma stream into a surrounding space substantially radially with respect to the opening of the outlet of the gas delivering device, wherein the guiding device comprises a concave surface at a surface facing the outlet of the gas-delivering device and a substantially hemispherical surface at a surface facing away from the outlet of the gas-delivering device, and wherein only the electrode and the guiding device, and no other portion, of the apparatus extend past the opening of said outlet at said furthest distal end of the gas-delivering device.

10. The apparatus of claim 9, wherein the guiding device is shaped such that damage to the tissue is prevented if the guiding device touches the tissue.

11. The apparatus of claim 9, wherein the electrode is configured such that it may be retracted and pushed forward with respect to the gas-delivering device.

12. The apparatus of claim 11, wherein when the electrode is in a fully retracted state, the guiding device is seated on the opening of said outlet at said furthest distal end of the gas-delivering device.

13. The apparatus of claim 9, wherein the guiding device is comprised of a ceramic.

14. An argon plasma coagulating probe assembly comprising:

a tube;

an electrode disposed substantially coaxially with the tube and configured to generate a high-frequency current, wherein a distal end of the electrode projects outward through an outlet of the tube; and a guiding device disposed at the distal end of the electrode, wherein the guiding device is configured for guiding an inert gas stream delivered from said outlet of the tube, wherein a cross-section of at least a portion of said guiding device is at least a size of an opening of said outlet at a furthest distal end of said tube in order to divert said inert gas stream substantially radially with respect to said opening of said outlet of said tube;

wherein the guiding device is comprised of an electrically insulating and thermally stable material and is configured to have a concave surface at a surface facing the outlet of the gas-delivering device and a substantially hemispherical surface at a surface facing away from the outlet of the gas-delivering device to prevent mechanical damage if the guiding device touches the tissue, and wherein only the electrode and the guiding device, and no other portion, of the argon plasma coagulating probe assembly extend past the opening of said outlet at said furthest distal end of the tube.

15. The argon plasma coagulating probe assembly of claim 14, wherein said electrode is movable relative to said outlet such that when said electrode is moved into a retracted position said guiding device closes said opening of said outlet in a substantially leakproof manner.

16. The argon plasma coagulating probe assembly of claim 14, wherein the guiding device is ceramic.

* * * * *